United States Patent [19]
Berg et al.

[11] Patent Number: 5,207,876
[45] Date of Patent: May 4, 1993

[54] SEPARATION OF TETRACHLOROETHYLENE FROM THE LOWER ALCOHOLS BY EXTRACTIVE DISTILLATION

[75] Inventors: Lloyd Berg, 1314 S. 3rd Ave., Bozeman, Mont. 59715; Zuyin Yang, Bozeman, Mont.

[73] Assignee: Lloyd Berg, Bozeman, Mont.

[21] Appl. No.: 822,141

[22] Filed: Jan. 17, 1992

[51] Int. Cl.$^5$ .................. B01D 3/40; C07C 17/38; C07C 29/84
[52] U.S. Cl. ............................. 203/57; 203/58; 203/60; 203/62; 203/63; 203/64; 568/913; 570/262
[58] Field of Search ............ 203/57, 60, 62, 63, 203/64, 58; 570/262; 568/913, 918

[56] References Cited

U.S. PATENT DOCUMENTS

| | | | |
|---|---|---|---|
| 4,036,703 | 7/1977 | Leroi et al. | 203/60 |
| 4,121,978 | 10/1978 | Becuwe | 203/60 |
| 5,118,392 | 6/1992 | Berg | 203/57 |
| 5,160,585 | 11/1992 | Berg | 203/57 |

Primary Examiner—Wilbur Bascomb, Jr.

[57] ABSTRACT

Tetrachloroethylene cannot be completely separated from methanol, ethanol, 1-propanol, isopropanol, 1-butanol, 2-butanol, isobutanol, 1-pentanol, 2-pentanol, 3-methyl-1-butanol or t-amyl alcohol by conventional distillation or rectification because of the minimum boiling azeotropes. Tetrachloroethylene can be readily separated from these alcohols by extractive distillation. A typical effective agent is dimethylsulfoxide.

14 Claims, No Drawings

SEPARATION OF TETRACHLOROETHYLENE FROM THE LOWER ALCOHOLS BY EXTRACTIVE DISTILLATION

FIELD OF THE INVENTION

This invention relates to a method for separating tetrachloroethylene from the lower alcohols using certain organic compounds as the agent in extractive distillation.

DESCRIPTION OF PRIOR ART

Extractive distillation is the method of separating close boiling compounds or azeotropes by carrying out the distillation in a multiplate rectification column in the presence of an added liquid or liquid mixture, said liquid(s) having a boiling point higher than the compounds being separated. The extractive agent is introduced near the top of the column and flows downward until it reaches the stillpot or reboiler. Its presence on each plate of the rectification column alters the relative volatility of the close boiling compounds in a direction to make the separation on each plate greater and thus require either fewer plates to effect the same separation or make possible a greater degree of separation with the same number of plates. When the compounds to be separated normally form an azeotrope, the proper agents will cause them to boil separately during the extractive distillation and thus make possible a separation in a rectification column that cannot be done at all when no agent is present. The extractive agent should boil higher than any of the close boiling liquids being separated and not form minimum azeotropes with them. Usually the extractive agent is introduced a few plates from the top of the column to insure that none of the extractive agent is carried over with lowest boiling component. This usually requires that the extractive agent boil twenty Centigrade degrees or more than the lowest boiling component.

At the bottom of a continuous column, the less volatile components of the close boiling mixtures and the extractive agent are continuously removed from the column. The usual methods of separation of these two components are the use of another rectification column, cooling and phase separation or solvent extraction.

Tetrachloroethylene, B.P.=121° C. forms minimum boiling azeotropes with the lower alcohols. With methanol, azeotrope boils at 63.7° C. and contains 37.5% tetrachloroethylene; with ethanol, the azeotrope boils at 76.7° C. and contains 37% tetrachloroethylene; with 1-propanol, the azeotrope boils at 94° C. and contains 52% tetrachloroethylene; with isopropanol, the azeotrope boils at 81.7° C. and contains 30% tetrachloroethylene; with 1-butanol, the azeotrope boils at 110° C. and contains 68% tetrachloroethylene; with 2-butanol, the azeotrope boils at 97° C. and contains 43% tetrachloroethylene; with isobutanol, the azeotrope boils at 103° C. and contains 60% tetrachloroethylene; with 1-pentanol, the azeotrope boils at 117° C. and contains 85% tetrachloroethylene; with 2-pentanol, the azeotrope boils at 113° C. and contains 66% tetrachloroethylene; with 3-methyl-2-butanol, the azeotrope boils at 116° C. and contains 81% tetrachloroethylene and with t-amyl alcohol, the azeotrope boils at 101° C. and contains 27% tetrachloroethylene.

Extractive distillation would be an attractive method of effecting the separation of tetrachloroethylene from these alcohols if agents can be found that (1) will enhance the relative volatility between tetrachloroethylene and these alcohols and (2) are easy to recover, that is, form no azeotrope with tetrachloroethylene or the alcohols and boil sufficiently above tetrachloroethylene and these alcohols to make separation by rectification possible with only a few theoretical plates.

Extractive distillation typically requires the addition of an equal amount to twice as much extractive agent as the tetrachloroethylene-alcohol mixture on each plate of the rectification column. The extractive agent should be heated to about the same temperature as the plate into which it is introduced. Thus, extractive distillation imposes an additional heat requirement on the column as well as somewhat larger plates. However this is less than the increase occasioned by the additional agents required in azeotropic distillation.

Another consideration in the selection of the extractive distillation agent is its recovery from the bottoms product. The usual method is by rectification in another column. In order to keep the cost of this operation to a minimum, an appreciable boiling point difference between the compound being separated and the extractive agent is desirable. We recommend twenty Centigrade degrees or more difference. It is also desirable that the extractive agent be miscible with the tetrachloroethylene and the alcohols otherwise it will form a two phase azeotrope with it and some other method of separation will have to be employed.

TABLE 1

Effect of Relative Volatility on the Separation of Tetrachloroethylene From Alcohols at 99% Purity

| Relative Volatility | Theoretical Plates | Actual Plates 75% Efficiency | Actual Plates 75% Eff., Min. Reflux |
|---|---|---|---|
| 1.2 | 50 | 67 | 87 |
| 1.5 | 23 | 31 | 40 |
| 2.0 | 13 | 17 | 22 |
| 3.0 | 9 | 12 | 16 |

The advantage of employing an effective extractive distillation agent is shown in Table 1. Tetrachloroethylene forms minimum boiling azeotropes with the lower alcohols which possess a relative volatility of 1.0 and cannot be separated by rectification. If extractive distillation is employed with an agent yielding a relative volatility of 2.0, a rectification column of only 22 actual plates will be required

OBJECTIVE OF THE INVENTION

The objects of this invention are to provide a process of method of extractive distillation that will enhance the relative volatility of tetrachloroethylene to methanol, ethanol, 1-propanol, isopropanol, 1-butanol, 2-butanol, isobutanol, 1-pentanol, 2-pentanol, 3-methyl-1-butanol and t-amyl alcohol in their separation in a rectification column. It is a further object of this invention to identify organic compounds that are stable, can be separated from tetrachloroethylene or the alcohols by rectification with relatively few plates and can be recycled to the extractive distillation column with little decomposition.

SUMMARY OF THE INVENTION

The objects of this invention are provided by a process for the separation of tetrachloroethylene from methanol, ethanol, 1-propanol, isopropanol, 1-butanol, 2-butanol, isobutanol, 1-pentanol, 2-pentanol, 3-methyl-1-butanol and t-amyl alcohol which entails the use of certain organic compounds as the agent in extractive distillation.

DETAILED DESCRIPTION OF THE INVENTION

We have discovered that certain organic compounds will effectively increase the relative volatility between tetrachloroethylene and methanol, ethanol, 1-propanol, isopropanol, 1-butanol, 2-butanol, isobutanol, 1-pentanol, 2-pentanol, 3-methyl-1-butanol or t-amyl alcohol when employed as the agent in extractive distillation.

The data in Tables 2, 3, 5, 6, 8, 9, 11, 12, 14, 15, 17, 18, 20, 21, 23, 25, 26, 28, 29, 31 and 32 was obtained in a vapor-liquid equilibrium still. In every case, the starting mixture was the tetrachloroethylene-alcohol azeotrope. The relative volatilities are listed for each of the agents.

Table 2 lists the compounds that we have found to be effective extractive distillation agents to recover tetrachloroethylene from methanol. They are dimethylsulfoxide, acetophenone, 2-heptanone, 3-heptanone, 5-methyl-2-hexanone, adiponitrile, 2-octanone, isophorone, 3,3-dimethyl-2-butanone, diisobutyl ketone, isobutyl heptyl ketone, 2,4-pentanedione, acetonyl acetone, methyl benzoate, methyl salicylate, hexyl formate, isobutyl butyrate, hexyl acetate, amyl propionate, ethyl n-valerate, ethylene glycol butyl ether acetate, ethylene glycol ethyl ether acetate, diethylene glycol ethyl ether acetate, phenyl acetate, propoxypropanol, butoxypropanol, dipropylene glycol methyl ether acetate, benzyl acetate, ethyl caproate and diethylene glycol diethyl ether.

Table 3 lists the compounds that were found to be ineffective agents for separating tetrachloroethylene from methanol.

TABLE 2

Effective Agents For Separating Tetrachloroethylene From Methanol

| Compounds | Relative Volatility |
| --- | --- |
| Dimethylsulfoxide | 1.45* |
| Acetophenone | 1.6 |
| 2-Heptanone | 1.8 |
| 3-Heptanone | 2.2 |
| 5-Methyl-2-hexanone | 1.7 |
| Adiponitrile | 1.2* |
| 2-Octanone | 2.8 |
| 3,3-Dimethyl-2-butanone | 1.65 |
| Diisobutyl ketone | 1.85 |
| Isobutyl heptyl ketone | 1.95 |
| 2,4-Pentanedione | 1.4 |
| Isophorone | 3.7 |
| Acetonyl acetone | 1.75 |
| Methyl benzoate | 1.6 |
| Methyl salicylate | 2.1 |
| Hexyl formate | 4.2 |
| Isobutyl butyrate | 3.8 |
| Hexyl acetate | 3.2 |
| Amyl propionate | 3.4 |
| Ethyl n-valerate | 1.85 |
| Ethylene glycol butyl ether acetate | 1.55 |
| Ethylene glycol ethyl ether acetate | 1.6 |
| Diethylene glycol ethyl ether acetate | 1.3 |
| Propoxypropanol | 1.3 |
| Butoxypropanol | 1.4 |
| Phenyl acetate | 1.55 |
| Dipropylene glycol methyl ether acetate | 1.2 |
| Benzyl acetate | 1.3 |
| Ethyl caproate | 2.1 |
| Diethylene glycol diethyl ether | 1.75 |

*Brings tetrachloroethylene out as overhead

TABLE 3

Ineffective Agents For Separating Tetrachloroethylene From Methanol

| | |
| --- | --- |
| Sulfolane | Dimethylformamide |
| 3-Octanone | Dimethylacetamide |
| Ethylene glycol diacetate | Glycerol triacetate |
| Propylene carbonate | 1-Methoxy-2-propanol acetate |

One of the agents, methyl benzoate, whose relative volatility had been determined in the vapor-liquid equilibrium still, was then evaluated in a glass perforated plate rectification column and the results listed in Table 4. Methyl benzoate gave a relative volatility of 1.44 after one hour and 1.62 after two hours of operation.

TABLE 4

Data From Run Made In Rectification Column

| Agent | Column | Time hrs. | Weight % $CCl_2-CCl_2$ | Weight % Methanol | Relative Volatility |
| --- | --- | --- | --- | --- | --- |
| Methyl benzoate | Overhead | 1 | 2.2 | 97.8 | 1.44 |
| | Bottoms | | 24.4 | 75.6 | |
| Methyl benzoate | Overhead | 2 | 0.6 | 99.4 | 1.62 |
| | Bottoms | | 17.7 | 82.3 | |

Table 5 lists the compounds that we have found to be effective extractive distillation agents to recover tetrachloroethylene from ethanol. They are dimethylsulfoxide, acetophenone, 5-methyl-2-hexanone, diisobutyl ketone, 2-heptanone, 3-heptanone, isobutyl heptyl ketone, 4-heptanone, 2,6-dimethyl-4-heptanone, 2-undecanone, 2,4-pentanedione, 2-octanone, 3-octanone, ethylene glycol methyl ether, diethylene glycol butyl ether, propoxypropanol, butoxypropanol, isophorone, methyl salicylate, diethylene glycol diethyl ether, 4-methyl-2-pentanol, n-decanol, methyl benzoate, amyl acetate, hexyl acetate, benzyl acetate, ethyl hexyl acetate, isobornyl acetate, amyl propionate, ethylene glycol butyl ether acetate, diethylene glycol ethyl ether acetate, isobutyl propionate, propyl caproate, ethyl valerate, diethyl malonate and hexyl formate.

Table 6 lists the compounds that we found to be ineffective agents for separating tetrachloroethylene from ethanol.

One of the agents, diisobutyl ketone, whose relative volatility had been determined in the vapor-liquid equilibrium still, was then evaluated in a glass perforated plate rectification column and the results listed in Table 7. Diisobutyl ketone gave a relative volatility of 1.35 after one hour and 1.62 after 1.5 hours of operation.

Table 8 lists the compounds that we have found to be effective extractive distillation agents to recover tetrachloroethylene from 1-propanol. They are dimethylsulfoxide, sulfolane, dimethylformamide, dimethylacetamide, 3-heptanone, 5-methyl-2-hexanone, adiponitrile, 2-octanone, diisobutyl ketone, 3-octanone, 2,4-pentanedione, isophorone, methyl benzoate, hexyl formate, isobutyl butyrate, hexyl acetate, amyl propionate, ethyl n-valerate, ethylene glycol butyl ether acetate, ethylene glycol ethyl ether acetate, butoxypropanol, phenyl acetate, dipropylene glycol methyl ether acetate, benzyl acetate, ethylene glycol diacetate, glycerol triacetate, triethylene glycol diacetate, diethylene glycol diethyl ether and propylene carbonate.

Table 9 lists the compound that we have found to be ineffective agents for separating tetrachloroethylene from 1-propanol.

TABLE 5

Effective Agents For Separating
Tetrachloroethylene From Ethanol

| Compounds | Relative Volatility |
|---|---|
| Dimethylsulfoxide | 1.4* |
| Acetophenone | 1.65 |
| 5-Methyl-2-hexanone | 1.55 |
| Diisobutyl ketone | 1.6 |
| 2-Heptanone | 1.55 |
| 3-Heptanone | 1.5 |
| Isobutyl heptyl ketone | 1.8 |
| 4-Heptanone | 1.6 |
| 2,6-Dimethyl-4-heptanone | 1.8 |
| 2-Undecanone | 2.0 |
| 2,4-Pentanedione | 1.3 |
| 2-Octanone | 1.3 |
| 3-Octanone | 1.5 |
| Ethylene glycol methyl ether | 1.4* |
| Diethylene glycol butyl ether | 1.2 |
| Propoxypropanol | 1.3 |
| Butoxypropanol | 1.2 |
| Isophorone | 1.45 |
| Methyl salicylate | 1.6 |
| Diethylene glycol diethyl ether | 1.3 |
| 4-Methyl-2-pentanol | 1.3 |
| n-Decanol | 1.2 |
| Methyl benzoate | 1.4 |
| Amyl acetate | 1.7 |
| Hexyl acetate | 1.75 |
| Benzyl acetate | 1.3 |
| Ethyl hexyl acetate | 1.5 |
| Isobornyl acetate | 1.3 |
| Ethylene glycol butyl ether acetate | 1.3 |
| Diethylene glycol ethyl ether acetate | 1.4 |
| Amyl propionate | 1.7 |
| Isobutyl butyrate | 1.9 |
| Propyl caproate | 1.4 |
| Ethyl valerate | 1.7 |
| Diethyl malonate | 1.25 |
| Hexyl formate | 1.8 |

*Brings out tetrachloroethylene as overhead

TABLE 6

Ineffective Agents For Separating
Tetrachloroethylene From Ethanol

| | |
|---|---|
| Sulfolane | Dimethylformamide |
| Dimethylacetamide | Adiponitrile |
| Ethylene glycol ethyl ether | Ethylene glycol butyl ether |
| Ethylene glycol phenyl ether | Diethylene glycol methyl ether |
| Isoamyl alcohol | Diethylene glycol ethyl ether |
| Propylene carbonate | Isooctyl alcohol |
| Tridecyl alcohol | Benzyl alcohol |
| Butyl-acetate | Tetrahydrofurfuryl alcohol |
| Propylene glycol phenyl ether | 1-Methoxy-2-propanol acetate |
| Diethyl maleate | 1-Methyl-2-pyrrolidinone |

TABLE 7

Data From Run Made In Rectification Column

| Agent | Column | Time hrs. | Weight % CCl$_2$—CCl$_2$ | Weight % Ethanol | Relative Volatility |
|---|---|---|---|---|---|
| Diisobutyl ketone | Overhead | 1 | 4.5 | 95.5 | 1.35 |
| | Bottoms | | 29.7 | 70.3 | |
| Diisobutyl ketone | Overhead | 1.5 | 1.4 | 98.6 | 1.62 |
| | Bottoms | | 32.7 | 67.3 | |

One of the agents, diisobutyl ketone, whose relative volatility had been determined in the vapor-liquid equilibrium still, was then evaluated in a glass perforated plate rectification column and the results listed in Table 10. Diisobutyl ketone gave a relative volatility of 1.15 after one hour and 1.46 after two hours of operation.

Table 11 lists the compounds that we have found to be effective extractive distillation agents to recover tetrachloroethylene from isopropanol. They are dimethylsulfoxide, acetophenone, diisobutyl ketone, 5-methyl-2-hexanone, 2-heptanone, 3-heptanone, 4-heptanone, isobutyl heptyl ketone, 2-octanone, 2,6-dimethyl-4-heptanone, methyl benzoate, 2-undecanone, 2,4-pentanedione, propiophenone, 3-octanone, acetonyl acetone, methyl salicylate, amyl acetate, 2-ethyl hexyl acetate, hexyl acetate, ethylene glycol butyl ether, benzyl acetate, dipropylene glycol methyl ether acetate, ethylene glycol phenyl ether, ethyl caproate, propyl butyrate, isobutyl butyrate, hexyl formate, ethyl isovalerate, isophorone, propoxypropanol and butoxypropanol.

Table 12 lists the compounds that we have found to be ineffective agents for separating tetrachloroethylene from isopropanol.

One of the agents, diisobutyl ketone, whose relative volatility had been determined in the vapor-liquid equilibrium still was then evaluated in a glass perforated plate rectification column and the results listed in Table 13. Diisobutyl ketone gave a relative volatility of 1.37 after one hour and 1.72 after 1.5 hours of operation.

TABLE 8

Effective Agents For Separating
Tetrachloroethylene From 1-Propanol

| Compounds | Relative Volatility |
|---|---|
| Dimethylsulfoxide | 2.6 |
| Sulfolane | 2.1 |
| Dimethylformamide | 2.0 |
| Dimethylacetamide | 1.9 |
| 3-Heptanone | 1.2* |
| 5-Methyl-2-hexanone | 1.7* |
| Adiponitrile | 1.6 |
| 2-Octanone | 1.25 |
| Diisobutyl ketone | 1.45 |
| 3-Octanone | 1.2 |
| 2,4-Pentanedione | 2.2 |
| Isophorone | 1.3 |
| Methyl benzoate | 1.25 |
| Hexyl formate | 1.9 |
| Isobutyl butyrate | 1.55 |
| Hexyl acetate | 1.6 |
| Amyl propionate | 1.3 |
| Ethyl n-valerate | 1.25 |
| Ethylene glycol butyl ether acetate | 1.35 |
| Ethylene glycol ethyl ether acetate | 1.45 |
| Butoxypropanol | 1.35 |
| Phenyl acetate | 1.55 |
| Dipropylene glycol methyl ether acetate | 1.55 |
| Benzyl acetate | 1.8 |
| Ethylene glycol diacetate | 1.2 |
| Glycerol triacetate | 1.2* |
| Triethylene glycol diacetate | 1.55 |
| Diethylene glycol diethyl ether | 1.55 |
| Propylene carbonate | 1.3* |

*Brings 1-propanol out as overhead

TABLE 9

Ineffective Agents For Separating
Tetrachloroethylene From 1-Propanol

| | |
|---|---|
| Acetophenone | 2-Heptanone |
| 3,3-Dimethyl-2-butanone | Isobutyl heptyl ketone |
| Acetonyl acetone | Methyl salicylate |
| Propoxypropanol | Diethylene glycol ethyl ether |
| 1-Methoxy-2-propanol acetate | acetate |

TABLE 10

Data From Run Made In Rectification Column

| Agent | Column | Time hrs. | Weight % CCl$_2$—CCl$_2$ | Weight % 1-Pro-panol | Relative Volatility |
|---|---|---|---|---|---|
| Diisobutyl ketone | Over-head | 1 | 26.5 | 73.5 | 1.15 |
|  | Bottoms |  | 51.4 | 48.6 |  |
| Diisobutyl ketone | Over-head | 1.5 | 5.6 | 94.4 | 1.46 |
|  | Bottoms |  | 48.7 | 51.3 |  |

Table 14 lists the compounds that we have found to be effective extractive distillation agents to recover tetrachloroethylene from 1-butanol. They are propoxypropanol, butoxypropanol, mesityl oxide, 1-methoxy-2propanol acetate, dipropylene glycol methyl ether, diethylene glycol ethyl ether, 1-methoxy-2propanol, ethylene glycol methyl ether, ethyl 3-ethoxypropionate, diethylene glycol methyl ether, ethylene glycol butyl ether, ethylene glycol ethyl ether, diethylene glycol butyl ether, propylene glycol methyl ether, propylene glycol isobutyl ether, 4-methoxy-4-methyl pentanone-2, ethylene glycol phenyl ether, dimethylsulfoxide, dimethylformamide, dimethylacetamide, acetophenone, adiponitrile, isophorone, hexyl acetate, hexyl formate and ethyl n-valerate.

Table 15 lists the compounds that we have found to be ineffective agents for separating tetrachloroethylene from 1-butanol.

One of the agents, dipropylene glycol methyl ether, whose relative volatility had been determined in the vapor-liquid equilibrium still was then evaluated in a glass perforated plate rectification column and the results listed in Table 16. Dipropylene glycol methyl ether gave a relative volatility of 1.2 after one hour and 1.72 after two hours of operation.

Table 17 lists the compounds that we have found to be effective extractive distillation agents to recover tetrachloroethylene from 2-butanol. They are ethyl valerate, ethyl butyrate, isobutyl butyrate, ethyl isovalerate, isobornyl acetate, hexyl acetate, isobutyl isobutyrate, ethylene glycol ethyl ether acetate, dipropylene glycol methyl ether acetate, ethylene glycol methyl ether, ethylene glycol ethyl ether, ethylene glycol hexyl ether, diethylene glycol hexyl ether, 4-methyl pentyl acetate-2, hexyl formate, diethylene glycol methyl ether, 4-methyl-2-pentanone and isophorone.

Table 18 lists the compounds that we have found to be ineffective agents for separating tetrachloroethylene from 2-butanol.

One of the agents, isobornyl acetate, whose relative volatility had been determined in the vapor-liquid equilibrium still was then evaluated in a glass perforated plate rectification column and the results listed in Table 19. Isobornyl acetate gave a relative volatility of 1.39 after one hour of operation.

TABLE 11

Effective Agents For Separating Tetrachloroethylene From Isopropanol

| Compounds | Relative Volatility |
|---|---|
| Dimethylsulfoxide | 1.3* |
| Acetophenone | 1.7 |
| 5-Methyl-2-hexanone | 1.55 |
| Diisobutyl ketone | 1.6 |
| 2-Heptanone | 2.1 |
| 3-Heptanone | 1.4 |

TABLE 11-continued

Effective Agents For Separating Tetrachloroethylene From Isopropanol

| Compounds | Relative Volatility |
|---|---|
| Isobutyl heptyl ketone | 1.4 |
| 4-Heptanone | 1.4 |
| 2-Octanone | 1.5 |
| 2,6-Dimethyl-4-heptanone | 1.4 |
| 2-Undecanone | 1.4 |
| 2,4-Pentanedione | 1.3 |
| Propiophenone | 1.4 |
| 3-Octanone | 1.2 |
| Acetonyl acetone | 2.0 |
| Methyl benzoate | 2.1 |
| Methyl salicylate | 1.5 |
| Amyl acetate | 1.8 |
| 2-Ethyl hexyl acetate | 1.6 |
| Hexyl acetate | 1.4 |
| Ethylene glycol butyl ether | 1.3 |
| Dipropylene glycol methyl ether acetate | 1.5 |
| Ethylene glycol phenyl ether | 1.4 |
| Benzyl acetate | 1.4 |
| Ethyl caproate | 1.8 |
| Propyl butyrate | 1.6 |
| Isobutyl butyrate | 1.5 |
| Hexyl formate | 1.3 |
| Ethyl isovalerate | 1.8 |
| Isophorone | 1.4 |
| Propoxypropanol | 1.3 |
| Butoxypropanol | 1.3 |

*Brings tetrachloroethylene out as overhead

TABLE 12

Ineffective Agents For Separating Tetrachloroethylene From Isopropanol

| | |
|---|---|
| Sulfolane | Dimethylformamide |
| Adiponitrile | Dimethylacetamide |
| Ethylene glycol phenyl ether | 4-Methoxy-4-methyl pentanone-2 |
| Ethylene glycol methyl ether | Diethylene glycol methyl ether |
| Diethylene glycol ethyl ether | Propylene glycol phenyl ether |
| Ethylene glycol ethyl ether | 1-Methyl-2-pyrrolidinone |

TABLE 13

Data From Run Made In Rectification Column

| Agent | Column | Time hrs. | Weight % CCl$_2$—CCl$_2$ | Weight % Iso-propanol | Relative Volatility |
|---|---|---|---|---|---|
| Diisobutyl ketone | Over-head | 1 | 3.1 | 96.9 | 1.37 |
|  | Bottoms |  | 24.3 | 75.7 |  |
| Diisobutyl ketone | Over-head | 1.5 | 0.6 | 99.4 | 1.72 |
|  | Bottoms |  | 23.7 | 76.3 |  |

TABLE 14

Effective Agents For Separating Tetrachloroethylene From 1-Butanol

| Compounds | Relative Volatility |
|---|---|
| Propoxypropanol | 1.5* |
| Butoxypropanol | 1.3* |
| 1-Methoxy-2-propanol acetate | 1.9 |
| Mesityl oxide | 1.25 |
| Dipropylene glycol methyl ether | 1.8 |
| Diethylene glycol ethyl ether | 1.5 |
| 1-Methoxy-2-propanol | 2.2 |
| Ethyl 3-ethoxypropionate | 2.8 |
| Diethylene glycol methyl ether | 1.8 |
| Ethylene glycol butyl ether | 1.35 |
| Ethylene glycol methyl ether | 2.4 |

TABLE 14-continued
Effective Agents For Separating Tetrachloroethylene From 1-Butanol

| Compounds | Relative Volatility |
| --- | --- |
| Ethylene glycol ethyl ether | 2.2 |
| Diethylene glycol butyl ether | 1.65 |
| Propylene glycol methyl ether | 2.1 |
| Propylene glycol isobutyl ether | 1.75 |
| 4-Methoxy-4-methyl pentanone-2 | 1.5 |
| Ethylene glycol phenyl ether | 1.45 |
| Dimethylsulfoxide | 3.6 |
| Dimethylformamide | 3.0 |
| Dimethylacetamide | 2.7 |
| Acetophenone | 1.3 |
| Adiponitrile | 1.2 |
| Isophorone | 1.4* |
| Hexyl acetate | 1.3 |
| Hexyl formate | 1.2 |
| Ethyl n-valerate | 1.5 |

*Brings 1-butanol out as overhead

TABLE 15
Ineffective Agents For Separating Tetrachloroethylene From 1-Butanol

| | |
| --- | --- |
| Hexyl acetate | Dipropylene glycol methyl ether acetate |
| Methyl isoamyl ketone | Ethylene glycol ethyl ether acetate |
| Ethylene glycol methyl ether | 4-Methoxy-2-pentanone |
| Diisobutyl ketone | 2,6-Dimethyl-4-heptanone |
| Sulfolane | 2-Heptanone |
| 3-Heptanone | 2-Octanone |
| Amyl acetate | Ethyl phenyl acetate |
| Benzyl acetate | Methyl benzoate |

TABLE 16
Data From Run Made In Rectification Column

| Agent | Column | Time hrs. | Weight % CCl$_2$—CCl$_2$ | Weight % 1-Butanol | Relative Volatility |
| --- | --- | --- | --- | --- | --- |
| Dipropylene glycol methyl ether | Overhead | 1 | 85.1 | 14.9 | 1.2 |
| | Bottoms | | 60.4 | 39.6 | |
| Dipropylene glycol methyl ether | Overhead | 2 | 98.9 | 1.1 | 1.72 |
| | Bottoms | | 62.2 | 37.8 | |

TABLE 17
Effective Agents For Separating Tetrachloroethylene From 2-Butanol

| Compounds | Relative Volatility |
| --- | --- |
| Ethyl valerate | 1.3 |
| Ethyl butyrate | 1.35 |
| Isobutyl butyrate | 1.5 |
| Ethyl isovalerate | 1.85 |
| Isobornyl acetate | 1.4 |
| Hexyl acetate | 1.35 |
| Isobutyl isobutyrate | 1.55 |
| Ethylene glycol ethyl ether acetate | 1.4 |
| Dipropylene glycol methyl ether acetate | 1.2 |
| Ethylene glycol methyl ether | 1.3* |
| Ethylene glycol ethyl ether | 1.2* |
| Ethylene glycol hexyl ether | 1.2* |
| Diethylene glycol hexyl ether | 1.25 |
| 4-Methyl pentyl acetate-2 | 1.25 |
| Hexyl formate | 1.3 |
| Diethylene glycol methyl ether | 1.75* |
| 4-Methyl-2-pentanone | 1.2* |
| Isophorone | 1.2* |

*Brings tetrachloroethylene out as overhead

TABLE 18
Ineffective Agents For Separating Tetrachloroethylene From 2-Butanol

| | |
| --- | --- |
| Ethylene glycol butyl ether | Diethylene glycol ethyl ether |
| Diethylene glycol butyl ether | Dipropylene glycol methyl ether |
| Propylene glycol methyl ether | Tripropylene glycol methyl ether |
| Propylene glycol isobutyl ether | 1-Methoxy-2-propanol acetate |
| Propoxypropanol | Butoxypropanol |
| Cyclohexanol | 2-Ethyl hexyl acetate |
| Methyl benzoate | Ethyl benzoate |
| Diethyl maleate | |

TABLE 19
Data From Run Made In Rectification Column

| Agent | Column | Time hrs. | Weight % CCl$_2$—CCl$_2$ | Weight % 2-Butanol | Relative Volatility |
| --- | --- | --- | --- | --- | --- |
| Isobornyl acetate | Overhead | 1 | 6.1 | 93.9 | 1.39 |
| | Bottoms | | 41.5 | 58.5 | |

Table 20 lists the compounds that we have found to be effective extractive distillation agents to recover tetrachloroethylene from isobutanol. They are ethyl valerate, ethyl isovalerate, ethyl butyrate, amyl acetate, hexyl formate, 4-methyl pentyl acetate-2, ethyl hexyl acetate, methyl caproate, methyl benzoate, ethyl benzoate, ethylene glycol butyle ether acetate, isobutyl butyrate, isobutyl isobutyrate, 1-methoxy-2-propanol acetate, 3-heptanone, isobutyl heptyl ketone, dimethylsulfoxide, dimethylformaide, acetophenone, dimethylacetamide and sulfolane.

Table 21 lists the compounds that we have found to be ineffective agents for separating tetrachloroethylene from isobutanol.

One of the agents, dimethylsulfoxide, whose relative volatility had been determined in the vapor-liquid equilibrium still was then evaluated in a glass perforated plate rectification column and the results listed in Table 22. Dimethylsulfoxide gave a relative volatility of 2.2 after one hour and 2.3 after two hours of operation. Table 23 lists the compounds that we have found to be effective extractive distillation agents to recover tetrachloroethylene from 1-pentanol. They are dimethylsulfoxide, sulfolane, dimethylformamide, dimethylacetamide, acetophenone, adiponitrile, 2-heptanone, 3-heptanone, 3-methyl-2-hexanone, 2-octanone, diisobutyl ketone, isobutyl heptyl ketone, 2,6-dimethyl-4-heptanone, 2,4-phentanedione, isophorone, acetonyl acetone, methyl benzoate, methyl salicylate, n-hexyl formate, hexyl acetate, isobutyl butyrate, amyl propionate, ethyl n-valerate, ethylene glycol butyl ether acetate, ethylene glycol ethyl ether acetate, diethylene glycol ethyl ether acetate, propoxypropanol, butoxypropanol, phenyl acetate, ethyl isovalerate, ethyl caproate, diethylene glycol diethyl ether, propylene carbonate and diethyl maleate.

One of the agents, diisobutyl ketone, whose relative volatility had been determined in the vapor-liquid equilibrium still was then evaluated in a glass perforated plate rectification column and the results listed in Table 24. Diisobutyl ketone gave a relative volatility of 1.45 after one hour and 1.36 after 1.5 hours of operation.

Table 25 lists the compounds that we have found to be effective extractive distillation agents to recover tetrachloroethylene from 2-pentanol. They are dimethylsulfoxide, sulfolane, dimethylformamide, dimethylacetamide, adiponitrile, diethylene glycol ethyl ether, diethylene glycol diethyl ether, 2,4-pentanedione, ethylene carbonate, propylene carbonate, 1-methyl-2-pyrrolidinone, triethylene glycol diacetate, diethylene glycol methyl ether, diethylene glycol butyl ether and propylene glycol isobutyl ether.

Table 26 lists the compounds that we have found to be ineffective agents for separating tetrachloroethylene from 2-pentanol.

TABLE 20

Effective Agents For Separating Tetrachloroethylene From Isobutanol

| Compounds | Relative Volatility |
| --- | --- |
| Ethyl valerate | 1.4 |
| Ethyl isovalerate | 1.55 |
| Ethyl butyrate | 2.9 |
| Amyl acetate | 1.3 |
| Hexyl formate | 1.3 |
| 4-Methyl pentyl acetate-2 | 2.6 |
| Ethyl hexyl acetate | 1.25 |
| Methyl caproate | 1.5 |
| Methyl benzoate | 1.3 |
| Ethyl benzoate | 1.25 |
| Ethylene glycol butyl ether acetate | 1.25 |
| Isobutyl butyrate | 1.55 |
| Isobutyl isobutyrate | 1.25 |
| 1-Methoxy-2-propanol acetate | 1.55* |
| 3-Heptanone | 1.25 |
| Isobutyl heptyl ketone | 1.35 |
| Dimethylsulfoxide | 2.3* |
| Dimethylformamide | 2.3* |
| Dimethylacetamide | 1.7* |
| Acetophenone | 1.4 |
| Sulfolane | 1.2* |

*Brings tetrachloroethylene out as overhead

TABLE 21

Ineffective Agents For Separating Tetrachloroethylene From Isobutanol

| | |
| --- | --- |
| n-Decanol | Nonyl alcohol |
| n-Octanol | Isophorone |
| Benzyl alcohol | Ethylene glycol ethyl ether acetate |
| Hexyl acetate | Isobornyl acetate |
| Ethyl acetoacetate | Ethyl 3-ethoxypropionate |
| Ethylene glycol diacetate | 5-Methyl-2-hexanone |
| 2-Octanone | 2-Undecanone |
| Nitromethane | |

TABLE 22

Data From Run Made In Rectification Column

| Agent | Column | Time hrs. | Weight % CCl₂—CCl₂ | Weight % Iso-butanol | Relative Volatility |
| --- | --- | --- | --- | --- | --- |
| Dimethyl-sulfoxide | Over-head | 1 | 99.5 | 0.5 | 2.2 |
| | Bottoms | | 33.9 | 66.1 | |
| Dimethyl-sulfoxide | Over-head | 2 | 99.6 | 0.4 | 2.3 |
| | Bottoms | | 38.0 | 62.0 | |

TABLE 23

Effective Agents For Separating Tetrachloroethylene From 1-Pentanol

| Compounds | Relative Volatility |
| --- | --- |
| Dimethylsulfoxide | 2.0 |
| Sulfolane | 1.8 |
| Dimethylformamide | 2.2 |
| Dimethylacetamide | 1.65 |
| Acetophenone | 2.3 |
| Adiponitrile | 2.1 |
| 2-Heptanone | 2.1 |
| 3-Heptanone | 1.7 |
| 3-Methyl-2-hexanone | 1.8 |

TABLE 23-continued

Effective Agents For Separating Tetrachloroethylene From 1-Pentanol

| Compounds | Relative Volatility |
| --- | --- |
| 2-Octanone | 1.8 |
| Diisobutyl ketone | 1.4 |
| Isobutyl heptyl ketone | 1.4 |
| 2,6-Dimethyl-4-heptanone | 1.5 |
| 2,4-Pentanedione | 1.7 |
| Isophorone | 1.4 |
| Acetonyl acetate | 1.6 |
| Methyl benzoate | 1.7 |
| Methyl salicylate | 1.8 |
| n-Hexyl formate | 1.7 |
| Hexyl acetate | 1.9 |
| Isobutyl butyrate | 1.5 |
| Amyl propionate | 2.0 |
| Ethyl n-valerate | 1.8 |
| Ethylene glycol butyl ether acetate | 1.3 |
| Ethylene glycol ethyl ether acetate | 1.2 |
| Diethylene glycol ethyl ether acetate | 1.3 |
| Propoxypropanol | 1.7 |
| Butoxypropanol | 1.3 |
| Phenyl acetate | 1.6 |
| Ethyl isovalerate | 2.1 |
| Ethyl caproate | 1.3 |
| Diethylene glycol diethyl ether | 1.2 |
| Propylene carbonate | 1.7 |
| Diethyl maleate | 1.7 |

TABLE 24

Data From Run Made In Rectification Column

| Agent | Column | Time hrs. | Weight % CCl₂—CCl₂ | Weight % 1-Pent-anol | Relative Volatility |
| --- | --- | --- | --- | --- | --- |
| Diisobutyl ketone | Over-head | 1 | 98.9 | 1.1 | 1.45 |
| | Bottoms | | 86.7 | 13.3 | |
| Diisobutyl ketone | Over-head | 1.5 | 98.6 | 1.4 | 1.36 |
| | Bottoms | | 88.3 | 11.7 | |

TABLE 25

Effective Agents For Separating Tetrachloroethylene From 2-Pentanol

| Compounds | Relative Volatility |
| --- | --- |
| Dimethylsulfoxide | 2.5 |
| Sulfolane | 1.35 |
| Dimethylformamide | 2.0 |
| Dimethylacetamide | 1.9 |
| Adiponitrile | 1.2 |
| Diethylene glycol ethyl ether | 1.25 |
| Diethylene glycol diethyl ether | 1.25 |
| 2,4-Pentanedione | 1.3 |
| Ethylene carbonate | 1.55 |
| Propylene carbonate | 1.25 |
| 1-Methyl-2-pyrrolidinone | 1.7 |
| Triethylene glycol diacetate | 1.35 |
| Diethylene glycol methyl ether | 2.1 |
| Diethylene glycol butyl ether | 1.8 |
| Propylene glycol isobutyl ether | 1.7 |

TABLE 26

Ineffective Agents For Separating Tetrachloroethylene From 2-Pentanol

| | |
| --- | --- |
| Acetophenone | 2-Heptanone |
| 3-Heptanone | Diisobutyl ketone |
| Isophorone | Ethylene glycol ethyl ether acetate |
| Hexyl formate | Methyl benzoate |
| Amyl propionate | Ethylene glycol diacetate |
| Triacetin | 2-Undecanone |
| Ethyl n-valerate | Hexyl acetate |

TABLE 26-continued

Ineffective Agents For Separating
Tetrachloroethylene From 2-Pentanol

Methyl salicylate

TABLE 27

Data From Run Made In Rectification Column

| Agent | Column | Time hrs. | Weight % CCl$_2$—CCl$_2$ | Weight % 2-Pentanol | Relative Volatility |
|---|---|---|---|---|---|
| Dimethyl-sulfoxide | Over-head | 1 | 99.4 | 0.6 | 2.5 |
|  | Bottoms |  | 17 | 83 |  |
| Dimethyl-sulfoxide | Over-head | 1.5 | 99.6 | 0.4 | 2.6 |
|  | Bottoms |  | 15.7 | 84.3 |  |

One of the agents, dimethylsulfoxide, whose relative volatility had been determined in the vapor-liquid equilibrium still was then evaluated in a glass perforated plate rectification column and the results listed in Table 27. Dimethylsulfoxide gave a relative volatility of 2.5 after one hour and 2.6 after 1.5 hours of operation. Table 28 lists the compounds that we have found to be effective extractive distillation agents to recover tetrachloroethylene from 3-methyl-1-butanol. They are dimethylsulfoxide, sulfolane, acetophenone, dimethylformamide, dimethylacetamide, adiponitrile, 2-heptanone, 3-heptanone, diisobutyl ketone, 2,6-dimethyl-4-heptanone, isophorone, acetonyl acetone, isobutyl butyrate, ethylene glycol ethyl ether acetate, diethylene glycol ethyl ether acetate, propoxypropanol, butoxypropanol, ethyl caproate, diethylene glycol diethyl ether and propylene carbonate.

Table 29 lists the compounds that we have found to be ineffective agents for separating tetrachloroethylene from 3-methyl-1-butanol.

One of the agents, diethylene glycol diethyl ether, whose relative volatility had been determined in the vapor-liquid equilibrium still was then evaluated in a glass perforated plate rectification column and the results listed in Table 30. Diethylene glycol diethyl ether gave a relative volatility of 1.24 after one hour and 1.31 after 1.5 hours of operation.

Table 31 lists the compounds that we have found to be effective extractive distillation agents to recover tetrachloroethylene from t-amyl alcohol. They are dimethylsulfoxide, sulfolane, adiponitrile, dimethylformamide, dimethylacetamide, 2-heptanone, diisobutyl ketone, methyl salicylate, hexyl acetate, amyl propionate, ethyl n-valerate, ethylene glycol ethyl ether acetate, 2-undecanone, 2,4-pentanedione, ethylene glycol diacetate, 1-methyl-2-pyrrolidinone, propylene carbonate and ethylene carbonate.

Table 32 lists the compounds that we have found to be ineffective agents for separating tetrachloroethylene from t-amyl alcohol.

One of the agents, dimethylsulfoxide, whose relative volatility had been determined in the vapor-liquid equilibrium still was then evaluated in a glass perforated plate rectification column and the results listed in Table 33. Dimethylsulfoxide gave a relative volatility of 1.74 after one hour and 2.0 after 1.5 hours of operation.

THE USEFULNESS OF THE INVENTION

The usefulness or utility of this invention can be demonstrated by referring to the data presented in Tables 2 to 33. All of the successful agents show that tetrachloroethylene can be separated from methanol, ethanol, 1-propanol, isopropanol, 1-butanol, isobutanol, 1-pentanol, 2-pentanol, 3-methyl-1-butanol and t-amyl alcohol by means of extractive distillation in a rectification column and that the ease of separation as measured by relative volatility is considerable.

TABLE 28

Effective Agents For Separating
Tetrachloroethylene From 3-Methyl-1-butanol

| Compounds | Relative Volatility |
|---|---|
| Dimethylsulfoxide | 2.7 |
| Sulfolane | 1.6 |
| Dimethylformamide | 2.1 |
| Dimethylacetamide | 2.6 |
| Acetophenone | 1.7 |
| Adiponitrile | 1.8* |
| 2-Heptanone | 1.55 |
| 3-Heptanone | 1.9 |
| Diisobutyl ketone | 1.25* |
| 2,6-Dimethyl-4-heptanone | 1.25 |
| Isophorone | 1.45 |
| Acetonylacetone | 1.8 |
| Isobutyl butyrate | 1.3* |
| Ethylene glycol ethyl ether acetate | 2.15 |
| Diethylene glycol ethyl ether acetate | 1.35 |
| Propoxypropanol | 1.5 |
| Butoxypropanol | 1.7 |
| Ethyl caproate | 1.45* |
| Diethylene glycol diethyl ether | 1.9 |
| Propylene carbonate | 1.8 |

*Brings 3-Methyl-1-butanol out as overhead

TABLE 29

Ineffective Agents For Separating
Tetrachloroethylene From 3-Methyl-1-butano

| | |
|---|---|
| 2-Octanone | 5-Methyl-2-hexanone |
| Methyl benzoate | Isobutyl heptyl ketone |
| Methyl salicylate | n-Hexyl formate |
| Hexyl acetate | Amyl propionate |
| Propyl acetate | Ethylene glycol butyl ether acetate |
| Ethyl valerate | Diethyl maleate |

TABLE 30

Data From Run Made In Rectification Column

| Agent | Column | Time hrs. | Weight % CCl$_2$—CCl$_2$ | Weight % 3-Me-1-BuOH | Relative Volatility |
|---|---|---|---|---|---|
| Diethylene glycol diethyl ether | Over-head | 1 | 93.0 | 7.0 | 1.24 |
|  | Bottoms |  | 73.2 | 26.8 |  |
| Diethylene glycol diethyl ether | Over-head | 1.5 | 95.3 | 4.7 | 1.31 |
|  | Bottoms |  | 73.9 | 26.1 |  |

TABLE 31

Effective Agents For Separating
Tetrachloroethylene From t-Amyl Alcohol

| Compounds | Relative Volatility |
|---|---|
| Dimethylsulfoxide | 2.0 |
| Sulfolane | 1.45 |
| Dimethylformamide | 1.7 |
| Dimethylacetamide | 1.55 |
| Adiponitrile | 1.3* |
| 2-Heptanone | 1.25* |
| Diisobutyl ketone | 1.2* |
| Methyl salicylate | 1.2* |
| Hexyl acetate | 1.2* |
| Amyl propionate | 1.2* |
| Ethyl n-valerate | 1.2* |
| Ethylene glycol ethyl ether acetate | 1.2* |

TABLE 31-continued

Effective Agents For Separating Tetrachloroethylene From t-Amyl Alcohol

| Compounds | Relative Volatility |
| --- | --- |
| 2-Undecanone | 1.25* |
| 2,4-Pentanedione | 2.6* |
| Ethylene glycol diacetate | 1.35* |
| 1-Methyl-2-pyrrolidinone | 1.45 |
| Propylene carbonate | 1.35 |
| Ethylene carbonate | 1.5 |

*Brings t-Amyl alcohol out as overhead

TABLE 32

Ineffective Agents For Separating Tetrachloroethylene From t-Amyl Alcohol

| | |
| --- | --- |
| Acetophenone | 3-Heptanone |
| 5-Methyl-2-hexanone | 2-Octanone |
| 4-Heptanone | Isophorone |
| Methyl benzoate | Hexyl formate |
| Phenyl acetate | Ethylene glycol butyl ether acetate |
| Propoxypropanol | Butoxypropanol |
| Isobutyl heptyl ketone | Triethylene glycol diacetate |
| Triacetin | |

TABLE 33

Data From Run Made In Rectification Column

| Agent | Column | Time hrs. | Weight % CCl$_2$—CCl$_2$ | Weight % t-Amyl Alcohol | Relative Volatility |
| --- | --- | --- | --- | --- | --- |
| Dimethyl-sulfoxide | Overhead | 1 | 83 | 17 | 1.74 |
| | Bottoms | | 7.7 | 92.3 | |
| Dimethyl-sulfoxide | Overhead | 1.5 | 90.1 | 9.9 | 2.0 |
| | Bottoms | | 5.3 | 94.7 | |

WORKING EXAMPLES

EXAMPLE 1

Seventy grams of the tetrachloroethylene-methanol azeotrope and 30 grams of methyl salicylate were charged to a vapor-liquid equilibrium still and refluxed for four hours. Analysis indicated a vapor composition of 27.3% tetrachloroethylene 72.7% methanol; a liquid composition of 44% tetrachloroethylene, 56% methanol which is a relative volatility of 2.1.

EXAMPLE 2

A solution comprising 250 grams of the tetrachloroethylene-methanol azeotrope was placed in the stillpot of a 7.3 theoretical plate glass perforated plate rectification column. When refluxing began, an extractive agent comprising methyl benzoate was pumped into the column at a rate of 15 ml/min. The temperature of the extractive agent as it entered the top of the column was 65° C. After establishing the feed rate of the extractive agent, the heat input to the tetrachloroethylene-methanol in the stillpot was adjusted to give a total reflux rate of 40 ml/min. After one hour of operation, overhead and bottoms samples were collected and analysed by gas chromatography. The overhead analysis was 97.8% methanol 2.2% tetrachloroethylene and the bottoms analysis was 75.6% methanol, 24.4% tetrachhloroethylene. This gives an average relative volatility of 1.44 for each theoretical plate. Analysis after two hours of operation gave an overhead of 99.4% methanol, 0.6% tetrachloroethylene and a bottoms of 82.3% methanol, 17.7% tetrachloroethylene which is a relative volatility of 1.62 for each theoretical plate. This data is presented in Table 4.

EXAMPLE 3

A solution comprising 250 grams of the tetrachloroethylene-ethanol azeotrope was placed in the stillpot of the 7.3 theoretical plate rectification column. When refluxing began and extractive agent comprising diisobutyl ketone was pumped into the top of the column at a rate of 15 ml/min. The temperature of the extractive agent as it entered the column was 70° C. After establishing the feed rate of the extractive agent, the heat input to the tetrachloroethylene-ethanol in the stillpot was adjusted to give a total reflux rate of 40 ml/min. After one hour of operation, overhead and bottoms samples were collected and analysed. The overhead analysis was 95.5% ethanol, 4.5% tetrachloroethylene and the bottoms analysis was 70.3% ethanol, 29.7% tetrachloroethylene. This gives an average relative volatility of 1.35 for each theoretical plate. After 1.5 hours of operation, the overhead analysis was 98.6% ethanol, 1.4% tetrachloroethylene, and the bottoms analysis was 67.3% ethanol, 32.7% tetrachloroethylene which is a relative volatility of 1.62. This data is presented in Table 7.

EXAMPLE 4

A solution comprising 250 grams of the tetrachloroethylene-1-propanol azeotrope was placed in the stillpot of a 7.3 theoretical plate glass perforated plate rectification column. When refluxing began, an extractive agent comprising diisobutyl ketone was pumped into the column at a rate of 15 ml/min. Tje temperature of the extractive agent as it entered the top of the column was 68° C. After establishing the feed rate of the extractive agent, the heat input to the tetrachloroethylene-1-propanol in the stillpot was adjusted to give a total reflux rate of 40 ml/min. After one hour of operation, overhead and bottoms samples were collected and analysed by gas chromatography. The overhead analysis was 73.5% 1-propanol, 26.5% tetrachloroethylene and the bottoms analysis was 48.6% 1-propanol, 51.4% tetrachloroethylene. This gives an average relative volatility of 1.15 for each theoretical plate. Analysis after 1.5 hours of operation gave an overhead of 94.4% 1-propanol 5.6% tetrachloroethylene and a bottoms of 51.3% 1-propanol, 48.7% tetrachloroethylene which is a relative volatility of 1.46 for each theoretical plate. This data is presented in Table 10.

EXAMPLE 5

A solution comprising 250 grams of the tetrachloroethylene-isopropanol azeotrope was placed in the stillpot of the 7.3 theoretical plate rectification column. When refluxing began and extractive agent comprising diisobutyl ketone was pumped into the top of the column at a rate of 15 ml/min. The temperature of the extractive agent as it entered the column was 65° C. After establishing the feed rate of the extractive agent, the heat input to the tetrachloroethylene-isopropanol in the stillpot was adjusted to give a total reflux rate of 40 ml/min. After one hour of operation, overhead and bottoms samples were collecte and analysed. The overhead analysis was 96.9% isopropanol, 3.1% tetrachloroethylene and the bottoms analysis was 75.7% isopropanol, 24.3% tetrachloroethylene. This gives an average relative volatility of 1.37 for each theoretical plate.

After 1.5 hours of operation, the overhead analysis was 99.4% isopropanol, 0.6% tetrachloroethylene and the bottoms analysis was 76.3% isopropanol, 23.7% tetrachloroethylene which is a relative volatility of 1.72. This data is presented in Table 13.

EXAMPLE 6

A solution comprising 250 grams of the tetrachloroethylene 1-butanol azeotrope was placed in the stillpot of a 7.3 theoretical plate glass perforated plate rectification column. When refluxing began, an extractive agent comprising dipropylene glycol methyl ether was put into the column at a rate of 15 ml/min. The temperature of the extractive agent as it entered the top of the column was 76° C. After establishing the feed rate of the extractive agent, the heat input to the tetrachloroethylene-1-butanol in the stillpot was adjusted to give a total reflux rate of 40 ml/min. After one hour of operation, overhead and bottoms samples were collected and analysed by gas chromatography. The overhead analysis was 14.9% 1-butanol, 85.1% tetrachloroethylene and the bottoms analysis was 39.6% 1-butanol, 60.4% tetrachhloroethylene. This gives an average relative volatility of 1.20 for each theoretical plate Analysis after two hours of operation gave an overhead of 1.12% 1-butanol 98.9% tetrachloroethylene and a bottoms of 37.8% 1-butanol, 62.2% tetrachloroethylene which is a relative volatility of 1.27 for each theoretical plate. This data is presented in Table 16.

EXAMPLE 7

A solution comprising 250 grams of the tetrachloroethylene 2-butanol azeotrope was placed in the stillpot of a 7.3 theoretical plate glass perforated plate rectification column. When refluxing began, an extractive agent comprising isobornyl acetate was pumped into the column at a rate of 15 ml/min. The temperature of the extractive agent as it entered the top of the column was 71° C. After establishing the feed rate of the extractive agent, the heat input to the tetrachloroethylene-2-butanol in the stillpot was adjusted to give a total reflux rate of 40 ml/min. After one hour of operation, overhead and bottoms samples were collected and analysed by gas chromatography. The overhead analysis was 93.9% 2-butanol, 6.1% tetrachloroethylene and the bottoms analysis was 58.5% 2-butanol, 41.5% tetrachhloroethylene. This gives an average relative volatility of 1.39 for each theoretical plate. This data is presented in Table 19.

EXAMPLE 8

A solution comprising 250 grams of the tetrachloroethylene isobutanol azeotrope was placed in the stillpot of the 7.3 theoretical plate rectification column. When refluxing began an extractive agent comprising dimethylsulfoxide was pumped into the top of the column at a rate of 15 ml/min. The temperature of the extractive agent as it entered the column was 75° C. After establishing the feed rate of the extractive agent, the heat input to the tetrachloroethylene-isobutanol in the stillpot was adjusted to give a total reflux rate of 40 ml/min. After one hour of operation, overhead and bottoms samples were collected and analysed. The overhead analysis was 0.5% isobutanol, 99.5% and the bottoms analysis was 66.1% isobutanol, 33.9% tetrachloroethylene. This gives an average relative volatility of 2.2 for each theoretical plate. After two hours of operation, the overhead analysis was 0.4% isobutanol, 99.6% tetrachloroethylene and the bottoms analysis was 62% isobutanol, 38% tetrachloroethylene which is a relative volatility of 2.3. This data is presented in Table 22.

EXAMPLE 9

A solution comprising 250 grams of the tetrachloroethylene 1-pentanol azeotrope was placed in the stillpot of the 7.3 theoretical plate rectification column. When refluxing began and extractive agent comprising diisobutyl ketone was pumped into the top of the column at a rate of 15 ml/min. The temperature of the extractive agent as it entered the column was 78° C. After establishing the feed rate of the extractive agent, the heat input to the tetrachloroethylene-1-pentanol in the stillpot was adjusted to give a total reflux rate of 40 ml/min. After one hour of operation, overhead and bottoms samples were collected and analysed. The overhead analysis was 1.1% 1-pentanol, 98.9% tetrachloroethylene and the bottoms analysis was 13.3% 1-pentanol, 86.7% tetrachloroethylene. This gives an average relative volatility of 1.45 for each theoretical plate. After 1.5 hours of operation, the overhead analysis was 1.4% 1-pentanol, 98.6% tetrachloroethylene and the bottoms analysis was 11.7% 1-pentanol, 88.3% tetrachloroethylene which is a relative volatility of 1.36. This data is presented in Table 24.

EXAMPLE 10

A solution comprising 250 grams of the tetrachloroethylene 2-pentanol azeotrope was placed in the stillpot of the 7.3 theoretical plate rectification column. When refluxing began an extractive agent comprising dimethylsulfoxide was pumped into the top of the column at a rate of 15 ml/min. The temperature of the extractive agent as it entered the column was 76° C. After establishing the feed rate of the extractive agent, the heat input to the tetrachloroethylene-2-pentanol in the stillpot was adjusted to give a total reflux rate of 40 ml/min. After one hour of operation, overhead and bottoms samples were collected and analysed. The overhead analysis was 0.6% 2-pentanol, 99.4% tetrachloroethylene and the bottoms analysis was 83% 2-pentanol, 17% tetrachloroethylene. This gives an average relative volatility of 2.5 for each theoretical plate. After 1.5 hours of operation, the overhead analysis was 0.4% 2-pentanol, 99.6% tetrachloroethylene and the bottoms analysis was 84.3% 2-pentanol, 15.7% tetrachloroethylene which is a relative volatility of 2.6. This data is presented in Table 27.

EXAMPLE 11

A solution comprising 250 grams of the tetrachloroethylene-2-methyl-1-butanol azeotrope was placed in the stillpot of the 7.3 theoretical plate rectification column. When refluxing began, an extractive agent comprising diethylene glycol diethyl ether was pumped into the top of the column at a rate of 15 ml/min. The temperature of the extractive agent as it entered the column was 75° C. After establishing the feed rate of the extractive agent, the heat input to the tetrachloroethylene-2-methyl-1-butanol in the stillpot was adjusted to give a total reflux rate of 40 ml/min. After one hour of operation, overhead and bottoms samples were collected and analysed by gas chromatography. The overhead analysis was 7% 2-methyl-1-butanol, 93% tetrachloroethylene and the bottoms analysis was 26.8% 2-methyl-1-butanol, 73.2% tetrachloroethylene. This gives an average relative volatility of 1.24 for each theoretical plate.

Analysis after 1.5 hours of operation gave an overhead of 4.7% 2-methyl-1-butanol, 95.3% tetrachloroethylene and a bottoms analysis of 26.1% 2-methyl-1-butanol, 73.9% tetrachloroethylene which is a relative volatility of 1.31 for each theoretical plate. This data is presented in Table 30.

EXAMPLE 12

A solution comprising 250 grams of the tetrachloroethylene-t-amyl alcohol azeotrope was placed in the stillpot of the 7.3 theoretical plate rectification column. When refluxing began an extractive agent comprising dimethylsulfoxide was pumped into the top of the column at a rate of 15 ml/min. The temperature of the extractive agent as it entered the column was 67° C. After establishing the feed rate of the extractive agent, the heat input to the tetrachloroethylene-t-amyl alcohol in the stillpot was adjusted to give a total reflux rate of 40 ml/min. After one hour of operation, overhead and bottoms samples were collected and analysed. The overhead analysis was 17% t-amyl alcohol, 83% tetrachloroethylene and the bottoms analysis was 92.3% t-amyl alcohol, 7.7% tetrachloroethylene. This gives an average relative volatility of 1.74 for each theoretical plate. After 1.5 hours of operation, the overhead analysis was 9.9% t-amyl alcohol, 90.1% tetrachloroethylene and the bottoms analysis was 94.7% t-amyl alcohol, 5.3% tetrachloroethylene which is a relative volatility of 2.0. This data is presented in Table 33.

We claim:

1. A method for recovering tetrachloroethylene from a mixture of tetrachloroethylene and methanol which comprises distilling a mixture of tetrachloroethylene and methanol in the presence of about one part of an extractive agent per part of tetrachloroethylene-methanol mixture, recovering the methanol as overhead product and obtaining the tetrachloroethylene and the extractive agent from the stillpot, wherein said extractive agent consists of one material selected from the group consisting of acetophenone, 2-heptanone, 3-heptanone, 5-methyl-2-hexanone, 2-octanone, 3,3-dimethyl-2-butanone, diisobutyl ketone, isobutyl heptyl ketone, 2,4-pentanedione, isophorone, acetonyl acetone, methyl benzoate, methyl salicylate, hexyl formate, isobutyl butyrate, hexyl acetate, amyl propionate, ethyl n-valerate, ethylene glycol butyl ether acetate, ethylene glycol ethyl ether acetate, diethylene glycol ethyl ether acetate, propoxypropanol, butoxypropanol, phenyl acetate, benzyl acetate dipropylene glycol methyl ether acetate, ethyl caproate and diethylene glycol diethyl ether.

2. A method for recovering tetrachloroethylene from a mixture of tetrachloroethylene and methanol which comprises distilling a mixture of tetrachloroethylene and methanol in the presence of about one part of an extractive agent per part of tetrachlooethylene-methanol mixture, recovering the tetrachloroethylene as overhead product and obtaining the methanol and the extractive agent from the stillpot, wherein said extractive agent is dimethylsulfoxide or adiponitrile.

3. A method for recovering tetrachloroethylene from a mixture of tetrachloroethylene and ethanol which comprises distilling a mixture of tetrachloroethylene and ethanol in the presence of about one part of an extractive agent per part of tetrachloroethylene-ethanol mixture, recovering the ethanol as overhead product and obtaining the tetrachloroethylene and the extractive agent from the stillpot, wherein said extractive agent consists of one material selected from the group consisting of acetophenone, 5-methyl-2-hexanone, diisobutyl ketone, 2-heptanone, 3-heptanone, isobutyl heptyl ketone, 4-heptanone, 2,6-dimethyl-4-heptanone, 2-undecanone, 2,4-pentanedione, 2-octanone, 3-octanone, diethylene glycol diethyl ether, diethylene glycol butyl ether, propoxypropanol, butoxypropanol, isophorone, methyl salicylate, 4-methyl-2-pentanol, n-decanol, methyl benzoate, amyl acetate, hexyl acetate, benzyl acetate, ethyl hexyl acetate, isobornyl acetate, ethylene glycol butyl ether acetate, diethylene glycol ethyl ether acetate, amyl propionate, isobutyl butyrate, propyl caproate, ethyl valerate, diethyl malonate and hexyl formate.

4. A method for recovering tetrachloroethylene from a mixture of tetrachloroethylene and ethanol which comprises distilling a mixture of tetrachloroethylene and ethanol in the presence of about one part of an extractive agent per part of tetrachloroethylene-ethanol mixture, recovering the tetrachloroethylene as overhead product and obtaining the ethanol and the extractive agent from the stillpot, wherein said extractive agent is dimethylsulfoxide or ethylene glycol methyl ether.

5. A method for recovering tetrachloroethylene from a mixture of tetrachloroethylene and 1-propanol which comprises distilling a mixture of tetrachloroethylene and 1-propanol in the presence of about one part of an extractive agent per part of tetrachloroethylene-1-propanol mixture, recovering the tetrachloroethylene as overhead product and obtaining the 1-propanol and the extractive agent from the stillpot, wherein said extractive agent consists of one material selected from the group consisting of dimethylsulfoxide, sulfolane, dimethylformamide, dimethylacetamide, adiponitrile, 2-octanone, diisobutyl ketone, 3-octanone 2,4-pentanedione, isophorone, methyl benzoate, hexyl formate, isobutyl butyrate, hexyl acetate, amyl propionate, ethyl n-valerate, phenyl acetate, ethylene glycol butyl ether acetate, ethylene glycol ethyl ether acetate, butoxypropanol, dipropylene glycol methyl ether acetate, benzyl acetate, ethylene glycol diacetate, triethylene glycol diacetate and diethylene glycol diethyl ether.

6. A method for recovering tetrachloroethylene from a mixture of tetrachloroethylene and 1-propanol which comprises distilling a mixture of tetrachloroethylene and 1-propanol in the presence of about one part of an extractive agent per part of tetrachloroethylene-1-propanol mixture, recovering the 1-propanol as overhead product and obtaining the tetrachloroethylene and the extractive agent from the stillpot, wherein said extractive agent consists of one material selected from the group consisting of 5-methyl-2-hexanone, 3-heptanone, glycerol triacetate and propylene carbonate.

7. A method for recovering tetrachloroethylene from a mixture of tetrachloroethylene and isopropanol which comprises distilling a mixture of tetrachloroethylene and isopropanol in the presence of about one part of an extractive agent per part of tetrachloroethylene-isopropanol mixture, recovering the isopropanol as overhead product and obtaining the tetrachloroethylene and the extractive agent from the stillpot, wherein said extractive agent consists of one material selected from the group consisting of acetophenone, 5-methyl-2-hexanone, diisobutyl ketone, 2-heptanone, 3-heptanone, isobutyl heptyl ketone, 4-heptanone, 2-octanone, 2,6-dimethyl-4-heptanone, 2-undecanone, 2,4-pentanedione, propiophenone, 3-octanone, acetonyl acetone, methyl benzoate, methyl salicylate, amyl acetate, 2- ethyl hexyl acetate, hexyl acetate, ethylene glycol butyl ether, ethylene glycol phenyl ether, dipropylene glycol methyl ether acetate, benzyl acetate, ethyl caproate, propyl butyrate, isobutyl butyrate, hexyl formate, ethyl isovalerate, isophorone, propoxypropanol and butoxypropanol.

8. A method for recovering tetrachloroethylene from a mixture of tetrachloroethylene and isopropanol which comprises distilling a mixture of tetrachloroethylene and isopropanol in the presence of about one part of an extractive agent per part of tetrachloroethylene-isopropanol mixture, recovering the tetrachloroethylene as overhead product and obtaining the isopropanol and the extractive agent from the stillpot, wherein said extractive agent is dimethylsulfoxide.

9. A method for recovering tetrachloroethylene from a mixture of tetrachloroethylene and 1-pentanol which comprises distilling a mixture of tetrachloroethylene and 1-pentanol in the presence of about one part of an extractive agent per part of tetrachloroethylene-1-pentanol mixture, recovering the tetrachloroethylene as overhead product and obtaining the 1-pentanol and the extractive agent from the stillpot, wherein said extractive agent consists of one material selected from the group consisting of dimethylsulfoxide, sulfolane, dimethylformamide, dimethylacetamide, acetophenone, adiponitrile, 2-heptanone, 3-heptanone, 3-methyl-2-hexanone, 2-octanone, diisobutyl ketone, isobutyl heptyl ketone, 2,6-dimethyl-4-heptanone, 2,4-pentanedione, isophorone, acetonyl acetone, methyl benzoate, methyl salicylate, n-hexyl formate, hexyl acetate, isobutyl butyrate, amyl propionate, ethyl n-valerate, ethylene glycol butyl ether acetate, ethylene glycol ethyl ether acetate, diethylene glycol ethyl ether acetate, propoxypropanol, butoxypropanol, phenyl acetate, ethyl isovalerate, ethyl caproate, diethylene glycol diethyl ether, propylene carbonate and diethyl maleate.

10. A method for recovering tetrachloroethylene from a mixture of tetrachloroethylene and 2-pentanol which comprises distilling a mixture of tetrachloroethylene and 2-pentanol in the presence of about one part of an extractive agent per part of tetrachloroethylene-2-pentanol mixture, recovering the tetrachloroethylene as overhead product and obtaining the 1-pentanol and the extractive agent from the stillpot, wherein said extractive agent consists of one material selected from the group consisting of dimethylsulfoxide, sulfolane, dimethylformamide, dimethylacetamide, adiponitrile, diethylene glycol ethyl ether, diethylene glycol diethyl ether, 2,4-pentanedione, ethylene carbonate, propylene carbonate, 1-methyl-2-pyrrolidinone, triethylene glycol diacetate, diethylene glycol methyl ether, diethylene glycol butyl ether and propylene glycol isobutyl ether.

11. A method for recovering tetrachloroethylene from a mixture of tetrachloroethylene and 2-methyl-1-butanol which comprises distilling a mixture of tetrachloroethylene and 2-methyl-1-butanol in the presence of about one part of an extractive agent per part of tetrachloroethylene-2-methyl-1-butanol mixture, recovering the tetrachloroethylene as overhead product and obtaining the 2-methyl-1-butanol and the extractive agent from the stillpot, wherein said extractive agent consists of one material selected from the group consisting of sulfolane, dimethylsulfoxide, dimethylformamide, dimethylacetamide, acetophenone, 2-heptanone, 3-heptanone, 2,6-dimethyl-4-heptanone, isophorone, acetonyl acetone, ethylene glycol ethyl ether acetate, diethylene glycol ethyl ether acetate, propoxypropanol, butoxypropanol, diethylene glycol diethyl ether and propylene carbonate.

12. A method for recovering tetrachloroethylene from a mixture of tetrachloroethylene and 2-methyl-1-butanol which comprises distilling a mixture of tetrachloroethylene and 2-methyl-1-butanol in the presence of about one part of an extractive agent per part of tetrachloroethylene-2-methyl-1-butanol mixture, recovering the 2-methyl-1-butanol as overhead product and obtaining the tetrachloroethylene and the extractive agent from the stillpot, wherein said extractive agent consists of one material selected from the group consisting of adiponitrile, diisobutyl ketone, isobutyl butyrate and ethyl caproate.

13. A method for recovering tetrachloroethylene from a mixture of tetrachloroethylene and t-amyl alcohol which comprises distilling a mixture of tetrachloroethylene and t-amyl alcohol in the presence of about one part of an extractive agent per part of tetrachloroethylene-t-amyl alcohol mixture, recovering the tetrachloroethylene as overhead product and obtaining the t-amyl alcohol and the extractive agent from the stillpot, wherein said extractive agent consists of one material selected from the group consisting of dimethylsulfoxide, sulfolane, dimethylformamide, dimethlacetamide, 1-methyl-2-pyrrolidinone, propylene carbonate and ethylene carbonate.

14. A method for recovering tetrachloroethylene from a mixture of tetrachloroethylene and t-amyl alcohol which comprises distilling a mixture of tetrachloroethylene and t-amyl alcohol in the presence of about one part of an extractive agent per part of tetrachloroethylene-t-amyl alcohol mixture, recovering t-amyl alcohol as overhead product and obtaining the tetrachloroethylene and the extractive agent from the stillpot, wherein said extractive agent consists of one material selected from the group consisting of adiponitrile, 2-heptanone, diisobutyl ketone, methyl salicylate, hexyl acetate, amyl propionate, ethyl n-valerate, ethylene glycol ethyl ether acetate, 2-undecanone, 2,4-pentanedione and ethylene glycol diacetate.

* * * * *